United States Patent [19]

Lee

[11] Patent Number: 5,196,214
[45] Date of Patent: Mar. 23, 1993

[54] WATER SOLUBLE TEA EXTRACTS

[75] Inventor: Eldon C. Lee, New Milford, Conn.

[73] Assignee: Nestec S.A., Vevey, Switzerland

[21] Appl. No.: 806,812

[22] Filed: Dec. 6, 1991

Related U.S. Application Data

[63] Continuation of Ser. No. 534,978, Jun. 7, 1990, abandoned.

[51] Int. Cl.$^5$ .................................................. A23F 3/18
[52] U.S. Cl. ...................................... 426/52; 426/597
[58] Field of Search .................................. 426/52, 597

[56] References Cited

U.S. PATENT DOCUMENTS

| | | | |
|---|---|---|---|
| 4,483,876 | 11/1984 | Petersen | 426/52 |
| 4,668,525 | 5/1987 | Creswick | 426/597 |

FOREIGN PATENT DOCUMENTS

| | | |
|---|---|---|
| 0135222 | 3/1985 | European Pat. Off. . |
| 4617958 | 5/1971 | Japan . |
| 57-47465 | 3/1982 | Japan . |
| 59-34849 | 2/1984 | Japan . |
| 683709 | 9/1979 | U.S.S.R. . |
| 1459529 | 12/1976 | United Kingdom . |

OTHER PUBLICATIONS

English Language Abstract of Japanese Patent Number 7114958 (1971).
English Language Abstract of Soviet Patent 683709 (1985).
English Language Abstract of German Patent 2229401 (1972).
English Language Abstract of Japanese Patent 7110919 (1971).

*Primary Examiner*—Joseph Golian
*Attorney, Agent, or Firm*—Vogt & O'Donnell

[57] ABSTRACT

To increase the yield of soluble solids obtained from tea leaves for preparing instant teas, spent tea residues obtained from tea leaves extracted by a hot aqueous medium are hydrolyzed with cellulase in water to obtain an aqueous extract containing soluble hydrolyzed spent tea residue. To increase yield further, insoluble residue separated from the extract obtained from the cellulase hydrolysis is hydrolyzed with a protease in water to obtain an extract containing further soluble hydrolyzed spent tea residue.

5 Claims, No Drawings

WATER SOLUBLE TEA EXTRACTS

CROSS REFERENCE TO RELATED APPLICATION

This is a continuing application of Application Ser. No. 07/534,978, filed Jun. 7, 1990, now abandoned.

BACKGROUND OF THE INVENTION

The present invention relates to the preparation of tea products and more particularly to water soluble tea extracts prepared by acid hydrolysis of the spent tea residues formed during the hot aqueous extraction of tea leaves in the production of water soluble tea extracts.

The products of tea have been increasingly marketed in the form of water-soluble tea extracts, usually in the form of dry powders. Substantial research activity has been directed to improve the quality of tea beverage, having a flavour and colour as close as possible to that obtained by brewing tea leaves. Another aspect of soluble tea manufacturing is to increase the yield of tea soluble solids.

Methods of obtaining tea extracts from tea leaves using a series of countercurrent stages or a two-stage extraction are well-known. Temperatures of aqueous extraction vary from room temperature to elevated temperatures as high as 180° C. with elevated pressures.

However, the predominantly remaining spent tea, i.e., tea extraction residue material, is currently discarded.

In U.S. Pat. No. 4,668,525, a method is described for treating the spent tea leaf from a tea extraction process which comprises acidifying the spent tea leaf to reduce the pH to within the range of about 2.0 to 3.0 and subjecting the acidified spent tea leaf to further extraction with aqueous solvent at pressures of about 80-100 psig and temperatures of about 140-170° C. for at least 4 minutes and separating the remaining tea leaf solids from the aqueous solvent to leave a high temperature/high pressure aqueous extract. However, the resulting extract was found to have an unacceptable bitter taste with a pruny off-flavour.

Methods have been described for treating raw tea ingredients by means of enzymes in order to obtain water soluble tea extracts. For instance, Japanese Patent No. 71017958 describes the extraction of tea with a protopectinase and cellulase, Japanese Patent No. 82047465 describes the production of cereal teas which comprises heating at 110-220° C., impregnating with an aqueous solution of amylase, protease or cellulase, heat-drying at 50-100° C. and roasting at 100-170° C., and Japanese Patent No. 84034849 describes the production of instant tea by extraction with a mixture of glutinous starch, alpha amylase and at least one enzyme selected from beta amylase, cellulase and protease. EUR-A-135222 describes a process of treating black tea before extraction with a solution of tannase and one or more cell wall digesting enzymes such as cellulase.

Russian Patent No. 683709 describes the treatment of tea waste by fermenting with a mixture of pectolytic and cellulolytic enzymes and afterwards adding amino acids and saccharose and extracting at 70° to 90° C.

SUMMARY OF THE INVENTION

It has been found that by hydrolysing spent tea solids with cellulase, soluble tea solids can be obtained in good yields with a desirable tea flavour and no objectionable off-flavour, preferably without the addition of extraneous materials which would lead to a product which is not 100% tea.

Accordingly, the present invention comprises a process for the preparation of water-soluble tea extracts from spent tea residues formed during the hot aqueous extraction of tea leaves in the production of water-soluble tea extracts which comprises hydrolysing the said spent tea residues with cellulase in an aqueous medium.

DETAILED DESCRIPTION OF THE INVENTION

The spent tea residues and water-soluble tea extracts may be obtained by conventional methods by the hot aqueous extraction of black or green tea leaves, for instance, using a series of countercurrent stages or a two-stage extraction. Temperatures of the aqueous extraction may vary from room temperature to up to 180° C. or more with elevated pressures.

The spent tea residues used for the hydrolysis may be wet or dehydrated and advantageously ground, for instance, to an average particle size of from 0.05 to 2.0 millimetres.

The hydrolysis with the cellulase may be carried out by incubating the spent tea residue in an aqueous medium at a temperature and pH suitable for cellulase hydrolysis. The temperature may be from 30-65° C. and preferably from 40° to 55° C. The pH may be from 3 to 7 and preferably from 4.0 to 6.0.

The duration of the hydrolysis may vary widely, for instance up to 1 week, but conveniently the hydrolysis is carried out over a period of from 2 to 48 hours, preferably from 4 to 36 hours and especially from 8 to 30 hours.

The amount of spent tea residue in the aqueous medium may be from 2% to 40% and preferably from 10% to 25% by weight based on the weight of the water. The amount of cellulase may be from 0.02% to 2.0% and preferably from 0.1% to 0.2% by weight based on the weight of the water. The amount of cellulase is conveniently from 0.1 to 10% and preferably from 0.5% to 1.5% by weight based on the weight of spent tea residue.

The incubation mixture is preferably well agitated, for instance, by stirring vigorously.

The CELLUCLAST enzyme may be obtained from any source and one convenient source is Celluclast (Novo Enzymes) which is a cellulase preparation made by submerged fermentation of a selected strain of the fungus, Trichoderma reesei. Other sources of cellulase are AMANO Cellulase derived from T.viride (Amano International Enzyme Co.), Genencor CYTOLASE 123 derived from T.reesei (Genencor Inc), and BIOCON BIOCELLULASE (Bicono USA Inc.)

After cellulase hydrolysis this mixture is preferably heated to deactivate the enzyme activity.

The aqueous extract containing soluble hydrolyzed spent tea residue may be separated from the insoluble residue conveniently by filtration and if desired, concentrated.

Optionally, the cellulase treated spent tea grounds may be further hydrolysed with a protease, for example a bacterial protease or a fungal protease, in an aqueous medium. The protease hydrolysis may be carried out over a period up to 48 hours, preferably from 12 to 36 hours. The temperature of the protease hydrolysis may be from 30° to 65° C. and preferably from 45° to 55° C.

The pH of the protease hydrolysis may be from 4 to 8.5 depending on the protease used. The amount of protease used may be from 0.025 to 5% and preferably from 0.05 to 2% by weight based on the weight of the cellulase treated spent tea residue. After protease hydrolysis, the mixture is preferably heated to deactivate the protease.

The aqueous extract containing soluble hydrolysed spent tea residue obtained from the protease hydrolysis also may then be separated from the insoluble residue, conveniently by filtration and if desired, concentrated.

The separated aqueous extracts contains soluble hydrolysed spent tea residue may be mixed with conventional tea extract, nature tea essence or enhancer and spray dried to a moisture content of below 5%, preferably below 4%, by weight.

The following EXAMPLES further illustrate the present invention.

EXAMPLE 1

Spent tea residues formed during the hot aqueous extraction of black tea leaves in the production of water-soluble tea extracts were dehydrated to a moisture content of 5.49% and then ground through No. 16 mesh 1.18 mm sieve using a Reitz mill. 240 g of the tea residue grounds were added to 1600 ml water and incubated in a reactor with good agitation at 50° C. and a pH of 5.23 with 2.4 g of CELLUCLAST 1.5 L (Novo Enzymes) having an activity of 1500 NCU/g. Samples were taken after 10 hours and 24 hours hydrolysis and each sample was heated at 95° C. for 20 minutes to inactivate the enzyme activity, cooled, filtered and washed with deionised water. The insoluble residue was dried in a vacuum oven at 70° C. overnight to a constant weight, the filtrate was evaporated over a water bath and dried in a vacuum oven at 70° C. overnight to a constant weight and the yields of soluble and insoluble matter were determined. The HPLC analysis of the tea residue CELLUCLAST hydrolysate shows in Table I below that the hydrolysis products are mainly glucose, cellobiose and higher glucose polymers.

TABLE I

| Composition | % Yield/Tea Residue Solids | |
|---|---|---|
| | 10 hours hydrolysis | 24 hours hydrolysis |
| Glucose | 3.8 | 4.6 |
| Cellobiose | 3.7 | 4.8 |
| Higher Glucose Polymers (by difference) | 10.3 | 10.6 |
| Total Soluble Matter | 17.8 | 20.0 |

The cellulase hydrolysate of tea residue showed a slight tea flavour and an overall blend taste with no objectionable off-flavour.

EXAMPLE 2

The filtrate of 17.8% yield formed by the process of Example 1 after 10 hours hydrolysis was concentrated to 40–45% solids using a rotary evaporator at 50° C. 12 parts of this concentrate were blended 85 parts of aqueous tea extracts having a solids content of 40–45% and 3 parts of 3-fold tea essence and spray dried to a moisture content below 4%.

0.20% parts of this spray dried product were formulated with 7 parts of sugar and 0.125 parts of citric acid and made up to 100 parts with water. This compounded tea sample had a good tea flavour with no off-flavour.

EXAMPLES 3 and 4

150 g of the dehydrated cellulase pre-treated spent tea residues formed by the process of Example 1 were added to 1 liter of water and incubated with good agitation at 50° C. for 24 hours at a pH shown in Table II adjusted with 1N sodium hydroxide, with 1.5 g of the bacterial or fungal protease also shown in Table II. The mixture was then heated to 95° C. for 30 minutes to inactivate the enzyme, and filtered to determine the soluble and insoluble components which are shown in Table II.

TABLE II

| | | Based on cellulase pretreated tea residue | |
|---|---|---|---|
| Protease | PH | Insoluble components % | Soluble components % |
| Bacterial protease (Miles HT - Proteolytic 200) | 7.0 | 94.3 | 5.7 |
| Fungal protease (Miles Fungal Protease 60,000) | 5.0 | 94.8 | 5.2 |

I claim:

1. A process for obtaining water-soluble tea extracts comprising hydrolyzing spent tea residues with cellulase in water at a temperature of from 30° C. to 65° C. and at a pH of from 3 to 7, wherein the spent tea residues have been obtained form tea leaves extracted with hot water, to obtain an aqueous extract containing soluble hydrolyzed spent tea residues, separating insoluble residue from the extract, hydrolyzing the insoluble residue with a protease in water to obtain a second aqueous extract containing soluble hydrolyzed spent tea residue and then separating the second extract from insoluble residue.

2. A process according to claim 1 wherein the spent tea residues to be hydrolzyed with the cellulase have a particle size of from 0.05 mm to 2 mm, the spent tea residues are in an amount of from 2% to 40% by weight based upon a weight of the water, the cellulase is in an amount of from 0.02% to 2.0% by weight based on a weight of the water and wherein the protease is in an amount of from 0.025% to 5% by weight of the residue obtained from the cellulose hydrolysis, and the insoluble residue obtained from the cellulase hydrolysis is hydrolyzed with the protease at a temperature of from 30° C. to 65° C. at a pH of from 4 to 8.5.

3. A process according to claim 2 wherein the cellulase hydrolysis temperature is from 40° C. to 55° C. and the protease hydrolysis temperature is from 45° C. to 55° C.

4. A process according to claim 1 wherein the spent tea residues, cellulase and water are agitated during the cellulase hydrolysis and wherein the insoluble residue, protease and water are agitated during the protease hydrolysis.

5. A process according to claim 1 further comprising heating the second extract and insoluble residue obtained from the protease hydrolysis to deactivate the protease prior to separating the second extract therefore from the insoluble residue.

* * * * *

UNITED STATES PATENT AND TRADEMARK OFFICE
CERTIFICATE OF CORRECTION

PATENT NO.   : 5,196,214
DATED        : March 23, 1993
INVENTOR(S)  : Eldon C. Lee It is certified that error appears in the above-indentified patent and that said Letters Patent is hereby corrected as shown below:

Column 2, line 55, "Bicono" should be --Biocon--.

Column 3, line 12, "extracts" should be --extract--, and

"contains" should be --containing--.

Column 4, line 32, "form" should be --from--.

Column 4, line 64, delete "therefore".

Signed and Sealed this

Seventh Day of December, 1993

*Attest:*

BRUCE LEHMAN

*Attesting Officer*   *Commissioner of Patents and Trademarks*